United States Patent [19]

Barbul

[11] Patent Number: 5,157,022

[45] Date of Patent: Oct. 20, 1992

[54] METHOD FOR REDUCING BLOOD CHOLESTEROL USING ARGININE

[76] Inventor: Adrian Barbul, 123 W. LanVale St., Baltimore, Md. 21217

[21] Appl. No.: 440,589

[22] Filed: Nov. 22, 1989

[51] Int. Cl.$^5$ .......................... A61K 37/02; C07K 5/06; C07K 5/08

[52] U.S. Cl. ........................................ 514/18; 514/19; 514/356; 514/561; 546/318

[58] Field of Search .................... 514/18, 19, 356, 561; 546/318

[56] References Cited

U.S. PATENT DOCUMENTS

| | | | |
|---|---|---|---|
| 2,965,542 | 12/1960 | Castaigne | 514/561 |
| 3,143,469 | 8/1964 | Debay et al. | 514/356 |
| 4,008,323 | 2/1977 | Cousse et al. | 514/561 |
| 4,058,558 | 11/1977 | Cousse et al. | 514/561 |

FOREIGN PATENT DOCUMENTS

| | | | |
|---|---|---|---|
| 925567 | 5/1963 | United Kingdom | 514/356 |
| 1494299 | 7/1975 | United Kingdom | |

OTHER PUBLICATIONS

Nutrition Reports International, Kohls et al. *Blood Serum Lipid Levels of Humans Given Arginine, Lysine and Trytophan Supplements without Food*, Jan. 1987, vol. 35, No. 1, pp. 5-13.

"Immune and Metabolic Effects of Arginine in the Surgical Patient" John M. Daly, M.D.; John Reynolds, M.B., Arleen Thom, M.D., Linda Kinsley, B.S.N.; Marianne Dietrick-Gallagher, M.S.N., Jian Shou, M.D., and Bruce Ruggieri, M.S.

"Arginine Stimulates Lymphocyte Immune Response in Healthy Human Beings" Adrian Barbul, M.D., Donato A. Sisto, M.D., Hannah L. Wasserkrug, B.A., and Gershen Efron, M.D.

"Blood Serum Lipid Levels of Humans Given Arginine, Lysine and Tryptophan Supplements Without Food" K. J. Kohls, C. Kies and H. M. Fox.

*Primary Examiner*—Lester L. Lee

[57] ABSTRACT

A method for reducing the level of cholesterol in the bloodstream of a human being in provided. The method comprises the administration to a human or arginine derivative compound, or a related amino acid or derivative. Daily doses of these compounds have been found to significantly reduce blood cholesterol level.

17 Claims, No Drawings

METHOD FOR REDUCING BLOOD CHOLESTEROL USING ARGININE

BACKGROUND OF THE INVENTION

This invention relates to a method for reducing the level of cholesterol in the bloodstream of a living being, and more particularly to the effect of administering to a living being dosages of arginine on blood cholesterol levels.

One of the leading causes of death in the United States is circulatory or heart disease. A major contributor to heart disease in many individuals is high cholesterol levels in the bloodstream. Normal or healthy levels of cholesterol in the bloodstream range from about 170 mg/1 to 230 mg/1, whereas levels above 250 mg/1–300 mg/1 (depending on age) are often considered dangerous and require the patient to undergo some type of medical treatment.

High cholesterol levels in a patient's bloodstream are dangerous since cholesterol tends to build up along the inner wall of the patient's arteries. If the build up occurs in an artery which supplies the heart or brain with blood, the patient runs the risk of having a myocardial infarction (heart attack), or cerebral infarction (stroke)

Accordingly, for patients who have a high cholesterol level in the bloodstream, it is desirable to reduce this level as much as possible One of the more common ways in which to reduce blood cholesterol is by limiting the amount of cholesterol in one's diet. Foods such as beef, pork, whole milk, and polysaturated oils (e.g., palm or coconut) have a high content of cholesterol. Therefore, for patients trying to reduce their dietary intake of cholesterol, these foods should be avoided For a large number of patients, decreasing dietary intake of cholesterol is often not enough in terms of reducing the patient's blood cholesterol. Through their physicians, these patients may be prescribed medication (typically orally ingested) which help reduce blood cholesterol levels. Commonly used medicines include nicotinic acid, clofibrate and derivatives, and more recently inhibitors of 3-hydroxy- 3-methyl glutaryl-coenzyme A reductase. However, many of these medicines have a number of side effects, such as increased non-cardiac fatalities, liver function abnormalities and muscle pains (myopathy).

In January, 1987, in an article entitled "Blood Serum Lipid Levels of Humans Using Arginine, Lysine and Tryptophan Supplements Without Food", published in Nutrition Reports International, the effect of giving arginine in conjunction with a low fat, low cholesterol diet was reported. The study revealed that the use of an arginine supplement in combination with a low cholesterol diet did, in fact, lower blood serum cholesterol and LDL cholesterol levels. However, in this study, the arginine supplement was not found to be as effective as the low fat, low cholesterol diet in terms of reducing blood cholesterol levels. In addition, the arginine supplement was given only at night time, within a few hours following the last dietary intake by the patient. Thus, the contribution of arginine alone to lowering cholesterol levels was not ascertainable since arginine was given to patients in conjunction with a low cholesterol diet.

Since arginine has very little, if any, side effects when orally ingested, it would be desirable to provide a method for reducing cholesterol using arginine or a derivative thereof, but without any restrictions on the patient with respect to dietary intake or the time of day in which the arginine must be taken.

SUMMARY OF THE INVENTION

Generally speaking, in accordance with the invention, a method for reducing the level of cholesterol in the bloodstream of a living being is provided. For human beings, the method comprises orally ingesting an arginine compound or an arginine derivative, or an arginine related amino acid or its derivative, on a daily basis in which the compound contains between about 1 and 30 grams of free arginine or arginine related amino acid. The method is carried out without requiring the patient to lower diet cholesterol. Moreover, the daily dosages of the arginine or arginine derivative compound, or related amino acid compound, may be taken at any time during the day, including during the patient's mealtime.

Accordingly, it is an object of the invention to provide an improved method for reducing the level of cholesterol in the bloodstream of a living being.

It is another object of the invention to use arginine for reducing bloodstream cholesterol.

Still another object of the invention is to provide a method for reducing the level of cholesterol in the bloodstream without having to restrict dietary intake.

Yet a further object of the invention is the use of arginine for reducing bloodstream cholesterol without restricting the time of day at which the arginine is orally ingested by the patient.

Still other objects and advantages of the invention will in part be obvious and will in part be apparent from the following specification.

The invention accordingly comprises the steps exemplified in the method hereinafter disclosed, and the scope of the invention will be indicated in the claims.

DETAILED DESCRIPTION OF THE PREFERRED EMBODIMENT

The inventive method for reducing the level of cholesterol in the bloodstream of a living being comprises orally ingesting an arginine or arginine derivative compound on a daily basis. The arginine or arginine derivative compound which is taken on a daily basis contains between about 10 mg/kg body weight (of said living being) and 500 mg/kg body weight (of said living being) of free arginine.

For humans, the arginine or arginine derivative compound most often is ingested orally on a daily basis and contains between about 1 and 30 grams of free arginine. The preferred amount of free arginine taken on a daily basis is between about 3 and 24 grams.

Suitable arginine and arginine derivative compounds include arginine salts such as arginine HCl, arginine aspartate and arginine nicotinate. Other arginine compounds or derivatives may be chosen from di-peptides which include arginine such as alanylarginine (ALA-ARG) valinyl-arginine (VAL-ARG), isoleucinyl-arginine, (ISO-ARG) and leucinyl-arginine (LEU-ARG), and tri-peptides which include arginine such as arginyl-lysinyl-glutamic acid (ARG-LYS-GLU) and argi-nyl-glysyl-arginine (ARG-GLY-ARG).

All of these arginine or arginine derivative compounds are examples only, and other suitable compounds may be used, including these which may be developed at a later time. With respect to any of these compounds, what is critical is the amount of total arginine that is present, and sometimes, the synergy between arginine and the molecules.

One of the arginine salts that is particularly advantageous is the ester arginine nicotinate, which is a newly discovered compound especially suited for reducing blood cholesterol in a living being. Arginine nicotinate (molecular weight 297.3) has the structural formula

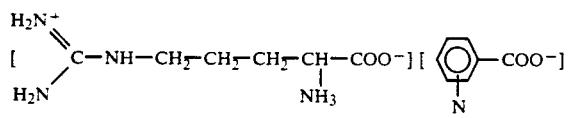

Arginine nicotinate combines the compounds nicotinic acid (also known as 3-pyridinecarboxylic acid or niacin) and arginine and is prepared for example as follows:

Preparation of Arginine Nicotinate 307.5g (2.5 mol) of nicotinic acid in 400 ml aqueous methanol are added to a suspension of 435 g (2.5 mol) of arginine base in 400 ml water. The resulting mixture is heated for one hour to form a solution which is concentrated in vacuo. The resulting yellow, oil residue is recrystallized from 1.5 l ethylacetate. The crystals are collected and then resuspended in diethylether. Thereafter, the crystals are recollected, washed with diethylether and dried in vacuo at 50 degrees C. Consequently, 450 g (61%) of arginine nicotinate are derived, having a melting point of between 163°-166 degrees C.

By using arginine nicotinate in accordance with this invention, the amounts of nicotinic acid and arginine normally required to be effective in reducing cholesterol levels in the blood may be somewhat reduced. This is because each compound has a different effect on cholesterol metabolism and its distribution and disposal in the body.

If arginine nicotinate is used, the daily dosage of arginine nicotinate contains between about 10 mg/kg body weight and 100 mg/kg body weight of free arginine.

If another salt or other compound or derivative of arginine is used, the daily dosage of that compound preferably contains between about 40 mg/kg body weight and 500 mg/kg body weight of free arginine.

As will be illustrated hereinafter, humans or animals who ingested an arginine or arginine derivative compound in accordance with the inventive method exhibited significantly reduced blood cholesterol levels even though these patients or animals were consuming a normal or cholesterol supplemented diet. In other words, the arginine or arginine derivative compounds were found to be effective even without a cholesterol lowering diet.

In addition, the method in accordance with the invention is not restricted in terms of the time of the day at which the arginine or arginine derivative compound must be ingested.

Furthermore, the method of deriving arginine derivates is not restricted by the examples given hereinbelow.

Alternatively, instead of an arginine or arginine derivative compound, the method of the invention may also be carried out using a related amino acid or derivative, such as the compound ornithine. Ornithine is an intermediate compound used in the metabolism of arginine.

In order to better illustrate the invention, the following examples are provided:

EXAMPLE 1

Twenty-four healthy human volunteers, divided into two groups, were chosen. One group (7 males/5 females, average age 31.9 years) received a daily oral supplement of 30 g of arginine HCl (24.8 g of free arginine) over 2 weeks. The other group of twelve (7 males/5 females, average age 31.4 years) received a daily supplement of 30 g of arginine of aspartate (17 g of free arginine) over 2 weeks. Both supplements were ingested throughout the day at the discretion of the subject. All subjects consumed a regular diet ad libitum, with no restrictions. None was taking any medications and all were non-smokers.

Using a hospital laboratory, blood lipid levels were determined for evaluation. Samples of blood were drawn at 8:00 a.m. after an overnight fast on day 1, 8 and 15 of the study. Day 1 represents baseline values prior to the beginning of the study.

|  | DAY 1 | DAY 8 | DAY 15 |
|---|---|---|---|
|  | Cholesterol | | |
| ArgHCl | 189.4 ± 10.9 | 160.3 ± 8.5 | 154.8 ± 7.2 |
| ArgAsp | 180.3 ± 9 | 162.7 ± 9.9 | 153.6 ± 5.9 |
|  | Triglycerides | | |
| ArgHCl | 94.8 ± 10.8 | 89.1 ± 9.1 | 69.5 ± 6.3 |
| ArgAsp | 89.6 ± 11.2 | 84.1 ± 17.9 | 94.3 ± 25.7 |

As shown, a significant drop in serum cholesterol was found in both treatment groups. In the group supplemented with arginine HCl, there was a 4.3±3.8% drop in serum cholesterol following one week of treatment and 17.3±3.0% after two weeks. Additionally, in the arginine HCl group, there was a marked drop in serum triglycerides.

As part of the study, LDL (low density lipids) and HDL (high density lipids) cholesterol levels in the bloodstream were determined for each group, as follows:

|  | DAY 1 | DAY 8 | DAY 15 |
|---|---|---|---|
|  | LDL | | |
| Arg HCl | 114.5 ± 8.1 | 99.3 ± 7.2 | 98.7 ± 7.2 |
| Arg Asp | 106.8 ± 9.8 | 98.6 ± 10.9 | 92.9 ± 7.4 |
|  | HDL | | |
| Arg HCl | 53.5 ± 4.6 | 48.3 ± 3.6 | 52.2 ± 3 |
| Arg Asp | 48.1 ± 3.2 | 46.3 ± 1.8 | 48.7 ± 2.4 |
|  | HDL/LDL | | |
| Arg HCl | 0.48 ± 0.04 | 0.50 ± 0.04 | 0.55 ± 0.04 |
| Arg Asp | 0.48 ± 0.05 | 0.52 ± 0.07 | 0.54 ± 0.05 |

As shown, there was a trend for LDL cholesterol to drop in both groups and for the HDL/LDL ratio to increase, both of which are desirable.

EXAMPLE 2

Six healthy human volunteers were given daily a one week oral supplementation of 30 g ornithine HCl (23.5 g of free ornithine). The volunteers did not undergo any dietary manipulation and were allowed to consume their normal diets. None was taking any medication. The supplements were given in the form of capsules to be ingested throughout the day.

Using a hospital laboratory, serum cholesterol levels in the blood of the volunteers were determined at the start of the study and after one week. Samples were analyzed by the hospital laboratory. The average serum cholesterol of the volunteers was 192.6±11.9 on day 0 and 156.1±7.3 on day 8.

A further example is illustrated in connection with an animal study.

EXAMPLE 3

Male CBA/J mice, 8-10 week old, average weight 21-23 grams, were fed a regular laboratory diet (19% protein, 4.6% fat content) which supports normal growth, reproduction and longevity. These mice also consumed either tap water or a solution of alanyl arginine lactate having a concentration of 15.2 g/l (8.3 g arginine/liter) [Assuming a 4 ml/mouse/day water intake, this translates into a diet supplement of 1.65 g arginine/kg body weight]. Both food and water were offered ad libitum. At the end of two weeks, plasma cholesterol was 207.3±10.9 in the controls and 158±12.3 in the treatment group. Further, no differences in weight gain or water intake were noted among the two groups.

EXAMPLE 4

Fifteen male Sprague Dawley rats, 8-9 week old, were placed on a 2% cholesterol, 0.3% cholic acid supplemented diet for 2 weeks. (This supplement will double normal rat cholesterol levels within two weeks). Then, 7 of the rats received 75 mg of arginine HCl intragastrically (by gavage) twice daily for one week, while the other 8 rats received equal volumes of water by gavage twice daily during that one week. All animals continued on the cholesterol-supplemented diet. After the one week of treatment was completed, all of the rats were sacrificed and plasma cholesterol, HDL, LDL and triglycerides levels were measured.

|  | Wt Gain (g) | Cholesterol |
|---|---|---|
| Control | 31.4 ± 7.1 | 140.6 ± 8.2 |
| Arg HCl | 24.6 ± 6.2 | 111.1 ± 6.6 |

|  | HDL | LDL | Triglycerides |
|---|---|---|---|
| Control | 29.9 ± 1.8 | 102 ± 8.7 | 43.5 ± 6.8 |
| Arg HCl | 28.6 ± 2.7 | 75.9 ± 8.5 | 32.9 ± 1.3 |

The data clearly demonstrates that arginine HCl can significantly reduce total cholesterol and LDL in spite of a high cholesterol intake. There was also a trend to reduce serum tri-glycerides levels, although this reduction did not achieve statistical significance.

EXAMPLE 5

Twenty male Sprague Dawley rates, 275-325 grams, were placed on 2% cholesterol, 0.3% cholic acid supplemented diet for two weeks. The rats were subjected to an overnight fast and then groups of 5 rats each received acute intraperitoneal injections of arginine HCl 100 mg/kg body weight, nicotinic acid 100 mg/kg body weight, arginine nicotinate 25 mg/kg body weight and control-saline respectively. Each of the drugs were administered in 2 ml volumes.

After 4 hours, samples of cardiac blood were obtained from the rats and serum cholesterol (mg %) and LDL (mg %) levels were measured.

| Saline | Arginine HCl | Nicotinic Acid | Arginine Nicotinate |
|---|---|---|---|
| Cholesterol | | | |
| 211.2 ± 32.7 | 118.4 ± 38.4 | 134.6 ± 15.9 | 112.6 ± 19.7 |
| LDL | | | |
| 146.2 ± 47.1 | 67.4 ± 12.1 | 68.6 ± 34.2 | 84.6 ± 12.5 |

The data clearly demonstrates that the administration of arginine HCl is effective in lowering elevated cholesterol and LDL levels, that arginine HCl is equally as effective as nicotinic acid (a well known cholesterol lowering agent, as discussed above) in lowering blood cholesterol levels, that arginine nicotinate is extremely effective in reducing serum cholesterol and LDL levels, and that arginine nicotinate is equally effective as arginine HCl and nicotinic acid if administered in one-fourth the amount. The latter suggests that arginine and nicotinic acid, when combined to form the salt arginine nicotinate, have a synergistic effect.

It will thus be seen that the objects set forth above, among those made apparent from the preceding description, are efficiently obtained, and since certain changes may be made in carrying out the above method without departing from the spirit and scope of the invention, it is intended that all matter contained in the above description shall be interpreted as illustrative and not in a limiting sense.

It is also to be understood that the following claims are intended to cover all the generic and specific features of the invention herein described and all statements of the scope of the invention which, as a matter of language, might be said to fall therebetween.

What is claimed is:

1. A method for reducing the level of cholesterol in the bloodstream of a human being comprising administering to said being a pharmaceutically effective amount of a compound selected from the group consisting of arginine nicotinate, and di and tri-peptides containing at least one arginine unit.

2. The method of claim 1, wherein said compound comprises arginine in an amount between about 1 and 30 grams per daily dosage.

3. The method of claim 2, wherein said arginine is an amount between about 3 and 24 grams per daily dosage.

4. The method of claim 1, wherein said compound is arginine nicotinate.

5. The method of claim 1, wherein said compound is selected from the group consisting of di and tri-peptides containing at least one arginine unit.

6. The method of claim 5, wherein said di and tri-peptides are selected consisting of alanyl-arginine, valinyl-arginine, isoleucinyl arginine, leucinyl arginine, arginyl-lysinyl-glutamic acid and arginyl-glysyl-arginine.

7. A method for treating high cholesterol in a living being comprising:
   administering to said living being a pharmaceutically effective amount of the compound selected from the group consisting of arginine nicotinate, di and tri-peptides containing at least one arginine unit and an ornithine HCl; and
   selectively measuring the level of serum cholesterol in the bloodstream of said living being.

8. The method of claim 7, wherein said compound is administered to said living being on a daily basis containing arginine in an amount between about 10 mg/kg body weight of said living being and 500 mg/kg body weight of said living being.

9. The method of claim 8, wherein said compound is arginine nicotinate, and wherein said arginine nicotinate is administered to said living being on a daily basis containing arginine in an amount between about 10 mg/kg body weight of said living being and 100 mg/kg body weight of said living being.

10. A compound suitable for reducing the level of cholesterol in a living being by the administration thereof of a pharmaceutically effective amount to said living being comprising arginine nicotinate.

11. The compound of claim 10, wherein said daily dosage of said arginine nicotinate contains arginine in an amount between about 10 mg/kg body weight of said living being and 100 mg/kg body weight of said living being.

12. A composition comprising an ester of arginine and nicotinic acid.

13. A method for reducing the level of cholesterol in the bloodstream of a living being comprising administering to said living being on a daily basis a compound selected from the group consisting of arginine nicotinate, di and tri-peptides containing at least one arginine unit and an ornithine HCl in an amount between about 10 mg/kg body weight of said living being and 500 mg/kg body weight of all living beings.

14. The method of claim 12, wherein said arginine or arginine derivative compound is selected from the group including arginine salts.

15. The method of claim 13, wherein said compound is arginine nicotinate.

16. The method of claim 15, wherein said di and tri-peptides are selected from the group consisting of alanyl-arginine, valinyl-arginine, isoleucinyl arginine, leucinyl arginine, arginyl-lysinyl-glutamic acid and arginyl-glysyl-arginine.

17. A method for reducing the level of blood cholesterol in a human being comprising administering to said being a pharmaceutically effective amount of an ornithine HCl.

* * * * *